United States Patent
Tatsumi et al.

(10) Patent No.: US 8,071,801 B2
(45) Date of Patent: Dec. 6, 2011

(54) PHOSPHORUS MOLYBDENUM COMPOUND AND METHOD FOR PRODUCING SAME

(75) Inventors: Yukio Tatsumi, Tokyo (JP); Kazuhiro Umehara, Tokyo (JP); Kenji Yamamoto, Tokyo (JP)

(73) Assignee: Adeka Corporation, Tokyo (JP)

( * ) Notice: Subject to any disclaimer, the term of this patent is extended or adjusted under 35 U.S.C. 154(b) by 319 days.

(21) Appl. No.: 12/309,179

(22) PCT Filed: Jul. 3, 2007

(86) PCT No.: PCT/JP2007/063296
§ 371 (c)(1),
(2), (4) Date: Jan. 9, 2009

(87) PCT Pub. No.: WO2008/007579
PCT Pub. Date: Jan. 17, 2008

(65) Prior Publication Data
US 2009/0192062 A1 Jul. 30, 2009

(30) Foreign Application Priority Data

Jul. 10, 2006 (JP) .................................. 2006-188948
Apr. 9, 2007 (JP) .................................. 2007-101757

(51) Int. Cl.
C07F 9/02 (2006.01)
C07F 9/09 (2006.01)
C10M 137/04 (2006.01)
C10M 133/16 (2006.01)
C10M 159/18 (2006.01)

(52) U.S. Cl. ............ 556/24; 556/26; 508/290; 508/362; 508/370; 508/379; 508/377

(58) Field of Classification Search .................. 508/290, 508/362, 370, 379; 556/24, 26
See application file for complete search history.

(56) References Cited

U.S. PATENT DOCUMENTS

2005/0107269 A1* 5/2005 Yagishita et al. ............. 508/440
2006/0111256 A1* 5/2006 Kinoshita et al. ............. 508/552

* cited by examiner

*Primary Examiner* — Walter D Griffin
*Assistant Examiner* — Vishal Vasisth
(74) *Attorney, Agent, or Firm* — Wenderoth, Lind & Ponack, L.L.P.

(57) ABSTRACT

Provided is a phosphorus molybdenum amine compound, represented by the following general formula (I).

$$R^6O-\overset{O}{\underset{O}{P}}-OR^5 \quad R^4O\underset{O}{\overset{O}{P}}OR^3$$
$$O=Mo-O-Mo\overset{}{-}_p O$$
$$O-Mo=O$$
$$R^2O-\overset{O}{\underset{O}{P}}-OR^1$$

(1)

where $R^1$ to $R^6$ each independently represent a hydrogen atom or a hydrocarbon group and p represents a number of 1 to 5, provided that all of $R^1$ to $R^6$ are can not all be hydrogen atoms at the same time and the phosphorus molybdenum compound is obtained by reducing a hexavalent molybdenum compound with a reducing agent, and then reacting the resulting with an acidic phosphate after neutralization with a mineral acid.

3 Claims, 4 Drawing Sheets

PHOSPHORUS MOLYBDENUM COMPOUND AND METHOD FOR PRODUCING SAME

This application is a 371 of PCT/JP2007/063296, filed Jul. 3, 2007.

TECHNICAL FIELD

The present invention relates to a phosphorus molybdenum compound, a method of producing a phosphorus molybdenum compound, a method of producing a phosphorus molybdenum amine compound using the phosphorus molybdenum compound, a phosphorus molybdenum amine compound obtained by the production method, and a lubricating oil composition containing the phosphorus molybdenum compound and/or the phosphorus molybdenum amine compound.

BACKGROUND ART

Various additives are added to lubricating oils such as engine oils, drive system oils, and metal working fluids for the purpose of enhancing the performances thereof. Various additives are available, but additives containing metals are generally used in many cases. If a metal is contained in a lubricating oil, for example, there arise problems such that the metal is released to the environment to cause various adverse effects, and a process for discharging the lubricating oil becomes complicated. Therefore, extensive studies have been made to develop a lubricating oil with as low a metal content as possible.

One of the most desirably replaced metal-containing additives is zinc dithiophosphate. Zinc dithiophosphate is an additive containing phosphorus and zinc atoms, but has antioxidant ability and abrasion resistance, and hence the compound is used in various lubricating oils. The reason why zinc dithiophosphate is so disliked is because the zinc dithiophosphate has various adverse effects as described above. However, among those, when the zinc dithiophosphate is added to automotive engine oil, phosphorus atoms released together with exhaust gas adhere to automotive exhaust gas catalysts, resulting in lowering the catalyst activity. If the catalyst activity is lowered, harmful substances such as nitrogen oxide and sulfur oxide contained in the exhaust gas may be released to the atmosphere without being decomposed by the exhaust gas catalyst.

However, if the amount of zinc dithiophosphate is reduced to a certain level or less, antioxidant ability is significantly degraded. Therefore, it was impossible to reduce the amount of zinc dithiophosphate below a certain level. Also, if the amount of an antioxidant such as a phenol-based antioxidant or an amine-based antioxidant is in place of the reduced amount zinc dithiophosphate, sludge in the lubricating oil increases as the lubricating oil deteriorates. Therefore, it was impossible to deal with the problem by increasing the amount of such antioxidants sdded.

Accordingly, antioxidant compositions having various compositions have been developed. For example, Patent Document 1 discloses an antioxidant system containing (A) a secondary diarylamine, (B) at least one sulfurized hindered phenol, and (C) an oil-soluble sulfur-containing molybdenum compound. Meanwhile, Patent Document 2 discloses a composition which contains a lubricating oil and at least a first antioxidant and a second antioxidant, and further the first antioxidant is a secondary diarylamine and the second antioxidant is 2,2,4-trialkyl-1,2-dihydroquinoline or a polymer thereof.

Patent Document 3 discloses a lubricating composition containing, as essential components, an oil-soluble molybdenum compound obtained by reacting one or two or more compounds selected from molybdenum trioxide, molybdic acid, and alkali salts thereof with a reducing agent, and then reacting the resultant compound with a monophosphate or a diphosphate, and a sulfur-containing compound.

Patent Document 1: JP 2001-089782 A
Patent Document 2: JP 2002-531632 A
Patent Document 3: JP 62-39696 A

DISCLOSURE OF THE INVENTION

Problems to be Solved by the Invention

However, in the antioxidant compositions as disclosed in Patent Document 1 or 2 above, it was impossible to reduce the amount of zinc dithiophosphate below a certain level, and as a result, the phosphorus content in a lubricating oil could not be reduced.

Meanwhile, the oil-soluble molybdenum compound described in Patent Document 3 is a product obtained by reducing a hexavalent molybdenum compound with a reducing agent, reacting the resultant with an acidic phosphorus compound, and neutralizing the resultant with a mineral acid. However, the oil-soluble molybdenum compound is essentially different from the phosphorus molybdenum compound obtained by the method of producing a phosphorus molybdenum compound of the present invention.

Therefore, an object of the present invention is to provide: a phosphorus molybdenum compound which can reduce the phosphorus content in a lubricating oil without impairing the antioxidant ability of the lubricating oil; a method of producing the compound; a method of producing a phosphorus molybdenum amine compound using the phosphorus molybdenum compound; a phosphorus molybdenum amine compound obtained by the method; and a lubricating oil composition which contains the phosphorus molybdenum compound and/or phosphorus molybdenum amine compound and has a lower phosphorus content.

Means for Solving the Problems

The inventors of the present invention have made extensive studies, thereby completing the present invention.

That is, the present invention includes a phosphorus molybdenum compound represented by the following general formula (I):

[Chemical Formula 1]

(1)

where $R^1$ to $R^6$ each independently represent a hydrogen atom or a hydrocarbon group, and p represents a number of 1 to 5, provided that all of $R^1$ to $R^6$ can not all be hydrogen atoms at the same time.

The phosphorus molybdenum compound can be produced by reducing a hexavalent molybdenum compound with a reducing agent; neutralizing the resultant with a mineral acid; and reacting the resultant with an acidic phosphate.

Further, the present invention includes a method of producing a phosphorus molybdenum amine compound including reacting the phosphorus molybdenum compound with an amine compound.

In addition, the present invention includes a phosphorus molybdenum amine compound obtained by the above method of producing a phosphorus molybdenum amine compound.

Further, the present invention includes a lubricating oil composition including the phosphorus molybdenum compound and/or the phosphorus molybdenum amine compound.

Effect of the Invention

The effect of the present invention is to provide a phosphorus molybdenum compound and a phosphorus molybdenum amine compound, which can reduce the phosphorus content in a lubricating oil without impairing the antioxidant effect of the lubricating oil.

BEST MODE FOR CARRYING OUT THE INVENTION

The novel phosphorus molybdenum compound of the present invention is a compound represented by the general formula (I):

[Chemical formula 2]

(1)

The phosphorus molybdenum compound has a cyclic structure formed by cyclization of pentavalent molybdenum, and the cyclic structure includes three or more molybdenum atoms. The value of p is a number of 1 to 5, and a cyclic structure including tetranuclear molybdenum with a p value of 2 is most easily formed. If the p value exceeds 5, it is estimated that the cyclic structure may become unstable. In addition, each molybdenum atom is bound to an acidic phosphate described below, and each of $R^1$ to $R^6$ is a group derived from the acidic phosphate, that is, a hydrogen atom or a group derived from the R group described below. All of $R^1$ to $R^6$ can not all be hydrogen atoms at the same time.

The phosphorus molybdenum compound of the present invention can serve as a high-performance antioxidant for a lubricating oil to attain both the long drain performance of a lubricating oil and the reduction of metal content. In addition, a phosphorus molybdenum amine compound obtained from the phosphorus molybdenum compound of the present invention can also act in the same way as above as a high-performance antioxidant for a lubricating oil. The phosphorus molybdenum compound and phosphorus molybdenum amine compound contain molybdenum and phosphorus atoms, and the addition of those compounds in small amounts can reduce the amount of another metal-containing additive, resulting in a significant reduction in the metal content as compared with a conventional lubricant.

The phosphorus molybdenum compound of the present invention can be produced by any production method. For example, the compound is preferably produced by: reducing a hexavalent molybdenum compound with a reducing agent; neutralizing the resultant with a mineral acid; and reacting the resultant with an acidic phosphate.

Here, examples of the hexavalent molybdenum compound that can be used in the production method for a phosphorus molybdenum compound of the present invention include metal salts of molybdic acid ($M_2MoO_4$, M represents a metal atom) such as molybdic trioxide, or hydrate thereof ($MoO_3 \cdot nH_2O$), molybdic acid ($H_2MoO_4$), sodium molybdate, and potassium molybdate and ammonium molybdate [$(NH_4)_2MoO_4$ or $(NH_4)_6(Mo_7O_{24}) \cdot 4H_2O$], $MOOCl_4$, $MOO_2Cl_2$, $MoO_2Br_2$, and $Mo_2O_3Cl_6$. Of those, molybdic trioxide or hydrate thereof, metal salts of molybdic acid, ammonium molybdate, and the like are preferred because of their easy availability.

Examples of the reducing agent that can be used in the production method for a phosphorus molybdenum compound of the present invention include sulfoxylic acid, dithionous acid (hydrosulfite), sulfurous acid, pyrosulfurous acid, thiosulfuric acid, dithionic acid, sulfinic acid, thiourea dioxide, or alkali metal salts or alkali earth metal salts thereof. Of those reducing agents, sulfinic acid, thiourea dioxide, or alkali metal salts or alkali earth metal salts thereof are preferred, and thiourea dioxide or alkali metal salts or alkali earth metal salts thereof are more preferred in view of their high reactivity.

The mineral acid that can be used in the production method for a phosphorus molybdenum compound of the present invention may be any one of a monobasic acid, a dibasic acid, a tribasic acid, and a partially neutralized product thereof. However, a mineral acid containing phosphorus atoms such as phosphoric acid can not be used. Examples of the mineral acid that can be used include hydrochloric acid, nitric acid, nitrous acid, sulfuric acid, sulfurous acid, perchloric acid, chloric acid, chlorous acid, and hypochlrous acid. From the viewpoint of reaction efficiency and production of a highly pure product, hydrochloric acid, nitric acid, and sulfuric acid are preferred. Further, nonvolatile compounds are preferred because of easy handling and use of sulfuric acid is particularly preferred.

The acidic phosphate to be used in the method of producing a phosphorus molybdenum compound of the present invention is a compound represented by the following general formula (2):

[Chemical Formula 3]

(2)

where R represents a hydrocarbon group, and m and n represent a number of 1 or 2, and m+n=3.

Examples of R in the general formula (2) include: alkyl groups such as a methyl group, an ethyl group, a propyl group, an isopropyl group, a butyl group, a tertiary butyl group, an amyl group, an isoamyl group, a hexyl group, a cyclohexyl group, a heptyl group, an isoheptyl group, an octyl group, an isooctyl group, a 2-ethylhexyl group, a nonyl group, an isononyl group, a decyl group, a dodecyl(lauryl) group, a tridecyl group, a tetradecyl(myristyl) group, a pentadecyl group, a hexadecyl(palmityl) group, a heptadecyl group, an octadecyl(stearyl) group; alkenyl groups such as a vinyl group, a 1-methylethenyl group, a 2-methylethenyl group, a propenyl group, a butenyl group, an isobutenyl group, a pentenyl group, a hexenyl group, a heptenyl group, an octenyl group, a decenyl group, a pentadecenyl group, an eicosenyl group, and a tricosenyl group; aryl groups such as a phenyl group, a nephthyl group, a 2-methylphenyl group, a 3-methylphenyl group, a 4-methylphenyl group, a 4-vinylphenyl group, a 3-isopropylphenyl group, a 4-isopropylphenyl group, a 4-butylphenyl group, a 4-isobutylphenyl group, a 4-tertiary butylphenyl group, a 4-hexylphenyl group, a 4-cyclohexylphenyl group, a 4-octylphenyl group, a 4-(2-ethylhexyl)phenyl group, and a 4-stearylphenyl group; and cycloalkyl groups such as a cyclohexyl group, a cyclopentyl group, a cyclohexyl group, a cycloheptyl group, a methylcyclopentyl group, a methylcyclohexyl group, a methylcycloheptyl group, a cyclopentenyl group, a cyclohexenyl group, a cycloheptenyl group, a methylcyclopetenyl group, a methylcyclohexenyl group, and a methylcycloheptenyl group.

Of those hydrocarbon groups, the alkyl and aryl groups are preferable because the compound is excellent in stability and produces no sludge when blended in a lubricating oil. Alkyl and aryl groups having 6 to 12 carbon atoms are more preferable in terms of the balance between solubility in a lubricating oil and the performance of the lubricating oil.

When the value of m in the general formula (2) is 1, the general formula (2) represents an acidic monophosphate, while when the value of m is 2, the general formula (2) represents an acidic diphosphate. The phosphate to be used in the present invention may be an acidic monophosphate or an acidic diphosphate, or a mixture thereof.

Those acidic phosphates can be prepared by reacting an alcohol represented by ROH with phosphoric acid, phosphorus pentoxide, or polyphosphoric acid. Preferably, the acidic phosphates are prepared by reacting the alcohol with phosphorus pentoxide because of the ease of the reaction. For example, the reaction may be performed by: gradually adding phosphorus pentoxide to an alcohol represented by ROH at 20 to 80° C. until the addition is completed; and aging the resultant at 40 to 120° C. for 1 to 10 hours. The reaction ratio of the alcohol represented by ROH and phosphorus pentoxide is as follows: phosphorus pentoxide:the alcohol=1 mol:2 to 4 mol, preferably 1 mol:2.5 to 3.5 mol.

Next, the method of producing a phosphorus molybdenum compound of the present invention will be described. Hexavalent molybdenum compounds used as materials are solid, and in order to reduce the compounds with a reducing agent, it is necessary to dissolve or disperse the compounds in water. A metal salt of molybdic acid such as sodium molybdate and ammonium molybdate are water-soluble and can be dissolved in water without further treatment. However, in the case where a water-insoluble molybdenum compound such as molybdenum trioxide is used, an alkaline agent may be added to dissolve the compound. Examples of the alkaline agent include: an alkali metal hydroxide such as lithium hydroxide, sodium hydroxide, or potassium hydroxide; and a basic nitrogen compound such as ammonia, monoethanolamine, diethanolamine, or triethanolamine. Of those, sodium hydroxide, potassium hydroxide, and ammonia are preferable because those compounds are easy to handle and inexpensive. The amount of water to be used for dissolution is not particularly limited as long as a hexavalent molybdenum compound can be dissolved or dispersed. The amount is preferably adjusted so that the solid content is 10 to 90% by mass. Meanwhile, the temperature for dissolution is 10 to 80° C., preferably 20 to 60° C., more preferably 20 to 40° C.

After the preparation of an aqueous solution or aqueous dispersion of the hexavalent molybdenum compound, it is necessary to reduce the compound with a reducing agent. The amount of the reducing agent is 0.1 to 2 mol, preferably 0.1 to 1 mol, and more preferably 0.2 to 0.8 mol, with respect to 1 mol of molybdenum in the aqueous solution. If the amount of the reducing agent is less than 0.1 mol, the compound cannot be reduced sufficiently, while if the amount exceeds 2 mol, economical disadvantages may be caused because the amount is excessive. The temperature in the system when the reducing agent is added is preferably 40 to 90° C., more preferably 50 to 80° C. After the addition of the reducing agent, the resultant may be stirred for 0.5 to 3 hours.

After the reduction of the hexavalent molybdenum compound, the resultant is neutralized with a mineral acid. In the case where the mineral acid is a monovalent acid, the addition amount of the mineral acid is 1 to 6 mol, preferably 2 to 5 mol, more preferably 3 to 5 mol with respect to 1 mol of molybdenum in the aqueous solution. In the case where the mineral acid is a divalent acid, the amount may be half the molar amount of the monovalent acid, while in the case where the mineral acid is a trivalent acid, the amount may be one-third of the molar amount of the monovalent acid. For example, the amount of the divalent acid is 0.5 to 3 mol, preferably 1 to 2.5 mol, more preferably 1.5 to 2.5 mol with respect to 1 mol of molybdenum in the aqueous solution. If the amount of the mineral acid is too small, the phosphorus molybdenum compound cannot be produced. If the amount of the mineral acid is too large, effects commensurate with the amount may not be achieved, and a post-treatment of the mineral acid may be difficult to perform. Meanwhile, the temperature in the system when the mineral acid is added is preferably 30 to 90° C., more preferably 40 to 80° C. Addition of the mineral acid produces heat due to heat of neutralization, and hence the mineral acid is gradually added for safety preferably over 0.1 to 3 hours, more preferably over 0.5 to 2 hours. After the addition, aging is performed at 30 to 90° C. for preferably 0.1 to 5 hours, more preferably 0.5 to 3 hours.

After the neutralization with the mineral acid, an acidic phosphate may be added to promote the reaction without further treatment. However, the addition of the acidic phosphate may increase the viscosity after the reaction or may cause precipitation of solid matter, and hence a solvent is preferably added before the addition of the acidic phosphate. The solvent to be used is not particularly limited as long as the solvent is non-aqueous. Examples of the solvent include: an aromatic-based solvent such as benzene, toluene, or xylene; an aliphatic hydrocarbon-based solvent such as hexane or petroleum ether; an ether-based solvent such as dimethyl ether or diethyl ether; and a ketone-based solvent such as methyl ethyl ketone. In addition, if the solvent may remain after all the reactions are made, a solvent that is difficult to remove (such as a mineral oil or a synthetic oil) may be used. Such a solvent is added in an amount of preferably 30 to 300 parts by mass, more preferably 50 to 200 parts by mass with respect to 100 parts by mass of the solid content in the system.

Thereafter, the acidic phosphate represented by the general formula (1) is added to the system to perform a reaction. In this step, the addition amount of the acidic phosphate is 0.5 to 2.5 mol, preferably 0.6 to 2 mol, more preferably 0.7 to 1.5 mol with respect to 1 mol of molybdenum in the system. If the amount of the acidic phosphate is too small, the compound of the present invention is not produced, while if the amount is too large, unreacted phosphates may remain. Meanwhile, the temperature of the system when the acidic phosphate is added is preferably 30 to 90° C., more preferably 40 to 80° C. The acidic phosphate is gradually added preferably over 0.1 to 3 hours, more preferably 0.5 to 2 hours. After the addition, aging is performed at 30 to 90° C., preferably 40 to 80° C. for 1 to 30 hours, more preferably 3 to 20 hours.

The phosphorus molybdenum compound can be produced by a reaction with an acidic phosphate, but the compound is preferably purified to increase the purity. The purification may be performed by any known method. Examples of the method include: a method involving removing water by distillation or the like and removing solid matter obtained as by-products by filtration; a method involving removing water and separating the phosphorus molybdenum compound of the present invention by distillation; and a method involving extracting the molybdenum compound of the present invention with an organic solvent. Of those purification methods, the method of purifying the compound with an organic solvent is preferable because of the ease of the purification process and high purity of the resultant compound.

Specifically, the method of purifying the compound with an organic solvent is performed by, for example, adding an organic solvent that separates from water in the system where the reaction has been completed, stirring the mixture, and allowing the resultant mixture to stand to separate into two phases. The aqueous phase may be the upper phase or the lower phase. In both the cases, the aqueous phase is removed, and then the organic solvent in the resultant organic solvent phase is removed under reduced pressure, to thereby produce the phosphorus molybdenum compound of the present invention. In order to reduce by-products or impurities, water is preferably further added to the resultant organic solvent phase to wash the phase.

The organic solvent that can be used may be any organic solvent that separates from water. Examples thereof include: aromatic-based solvents such as benzene, toluene, xylene, hemimellitene, pseudocumene, mesitylene, and cumene; aliphatic hydrocarbon-based solvents such as pentane, hexane, octane, and petroleum ether; ether-based solvents such as dimethyl ether and diethyl ether; and ketone-based solvents such as methyl ethyl ketone and methyl butyl ketone. Of those organic solvents, the aromatic-based solvent is preferably used, and benzene, toluene, and xylene are more preferably used because of the ease of separation into the aqueous phase and the organic phase. The amount of the organic solvent used is 20 to 400 parts by mass, preferably 50 to 200 parts by mass with respect to 100 parts by mass of the solid matters in the system. In the case where the solvent is used in the reaction, the amount of the solvent used should be controlled.

As described above, Patent Document 3 discloses a method of producing a phosphorus molybdenum compound similar to the method of producing a phosphorus molybdenum compound of the present invention. That is, the production method disclosed in Patent Document 3 involves: reducing a hexavalent molybdenum compound with a reducing agent; reacting the resultant with an acidic phosphorus compound; and neutralizing the resultant with a mineral acid. The difference between the production method of the present invention and the production method of Patent Document 3 is that the neutralization with the mineral acid is performed before and after the reaction of the reduced molybdenum compound with the acidic phosphate. The resultant phosphorus molybdenum compounds are different from each other, and the antioxidant ability is different from that of the phosphorus molybdenum compound of the present invention. Detailed data will be described in the Examples below.

The method of producing a phosphorus molybdenum amine compound of the present invention is characterized in that the above-mentioned phosphorus molybdenum compound of the present invention is reacted with an amine compound. The amine compound to be used in the method of producing a phosphorus molybdenum amine compound of the present invention is not particularly limited as long as the compound has a basic nitrogen atom. Examples thereof include an aliphatic amine, aromatic amine, alkanol amine, polyamine, or a reaction product of a fatty acid with a polyamine.

Examples of the aliphatic amines include alkyl amines such as (mono, di, tri)methyl amine, (mono, di, tri)ethyl amine, (mono, di, tri)propyl amine, (mono, di, tri)isopropyl amine, (mono, di, tri)butyl amine, (mono, di, tri)secondary butyl amine, (mono, di, tri)tertiary butyl amine, (mono, di, tri)pentyl amine, (mono, di, tri)isopentyl amine, (mono, di, tri)secondary pentyl amine, (mono, di, tri)tertiary pentyl amine, (mono, di, tri)hexyl amine, (mono, di, tri)secondary hexyl amine, (mono, di, tri)heptyl amine, (mono, di, tri)secondary heptyl amine, (mono, di, tri)octyl amine, (mono, di, tri) 2-ethylhexyl amine, (mono, di, tri)octyl amine, (mono, di, tri)secondary octyl amine, (mono, di, tri)nonyl amine, (mono, di, tri)secondary nonyl amine, (mono, di, tri)decyl amine, (mono, di, tri) secondary decyl amine, (mono, di, tri)undecyl amine, (mono, di, tri)secondary undecyl amine, (mono, di, tri)dodecyl amine, (mono, di, tri)secondary dodecyl amine, (mono, di, tri)tridecyl amine, (mono, di, tri)secondary tridecyl amine, (mono, di, tri)tetradecyl amine, (mono, di, tri) secondary tetradecyl amine, (mono, di, tri)hexadecyl amine, (mono, di, tri) secondary hexadecyl amine, (mono, di, tri) stearyl amine, (mono, di, tri)eicosyl amine, (mono, di, tri) docosyl amine; alkenyl amines such as vinyl amine, (mono, di, tri)allyl amine, (mono, di, tri)propenyl amine, (mono, di, tri)isopropenyl amine, (mono, di, tri)butenyl amine, (mono, di, tri)isobutenyl amine, (mono, di, tri)pentenyl amine, (mono, di, tri)isopentenyl amine, (mono, di, tri)hexenyl amine, (mono, di, tri)heptenyl amine, (mono, di, tri)octenyl amine, (mono, di, tri)nonenyl amine, (mono, di, tri)decenyl amine, (mono, di, tri)undecenyl amine, (mono, di, tri)dodecenyl amine, (mono, di, tri)tetradecenyl amine, and (mono, di, tri)oleyl amine.

In addition, examples of the aromatic amine include (mono, di, tri)phenyl amine, (mono, di, tri)tolyl amine, (mono, di, tri)xylylamine, (mono, di, tri)cumenylamine, (mono, di, tri)benzyl amine, (mono, di, tri)phenetyl amine, (mono, di, tri)styryl amine, (mono, di, tri)trityl amine, (mono, di, tri)ethylphenyl amine, (mono, di, tri)propylphenylamine, (mono, di, tri)butylphenylamine, (mono, di, tri)pentylphenylamine, (mono, di, tri)hexylphenylamine, (mono, di, tri)heptylphenyl amine, (mono, di, tri)octylphenyl amine, (mono, di, tri)nonylphenyl amine, (mono, di, tri)decylphenyl amine, (mono, di, tri)dodecylphenyl amine, (mono, di, tri) octadecylphenyl amine, (mono, di, tri)styrenatedphenylamine, (mono, di, tri)$_p$-cumylphenyl amine, (mono, di, tri)phenylphenyl amine, (mono, di, tri)benzylphenyl amine, (mono, di, tri)α-naphthyl amine, and (mono, di, tri)β-naphthyl amine.

Examples of the alkanol amine include (mono, di, tri) ethanol amine, (mono, di, tri)propanol amine, (mono, di, tri)isopropanol amine, (mono, di, tri)butanol amine, (mono, di, tri)pentanol amine, (mono, di, tri)hexanol amine, (mono, di, tri)octanol amine, (mono, di, tri)nonanol amine, (mono, di, tri)decanol amine, (mono, di, tri)dodecanol amine, (mono, di, tri)tridecanol amine, and (mono, di, tri)octadecanol amine.

In addition, examples of the polyamine include ethylene diamine, diethylene triamine, triethylene tetramine, tetraethylene pentamine, pentaethylene hexamine, propylene diamine, dipropylene triamine, tripropylene tetramine, tetrapropylene pentamine, and pentapropylene hexamine.

Further, examples of the fatty acid in the reaction product of a fatty acid with a polyamine include acetic acid, propionic acid, butanoic acid (butyric acid), pentanoic acid (valeric acid), isopentanoic acid (isovaleric acid), hexanoic acid (caproic acid), heptanoic acid, isoheptanoic acid, octanoic acid (caprylic acid), 2-ethylhexanoic acid, isooctanoic acid, nonanoic acid (peralgoic acid), isononanoic acid, decanoic acid (capric acid), isodecanoic acid, undecanoic acid, isoundecanoic acid, dodecanoic acid (lauric acid), isododecanoic acid, tridecanoic acid, isotridecanoic acid, tetradecanoic acid (myristic acid), hexadecanoic acid (palmitic acid), octadecanoic acid (stearic acid), isostearic acid, eicosanoic acid (arachic acid), docosanoic acid (behenic acid), tetracosanoic acid (lignoceric acid), hexacosanoic acid (cerotic acid), octacosanoic acid (montanic acid), 10-undecenic acid, zoomaric acid, oleic acid, elaidic acid, linoleic acid, linolenic acid, gadoleic acid, erucic acid, selacoleic acid, citric acid, succinic acid, fumaric acid, malic acid, and alkyl(alkenyl)succinic acid. By reaction of those fatty acids with the polyamine, the reaction product of a fatty acid and a polyamine can be obtained. Those reaction products may be amide compounds having amino groups and imide compounds having amino groups.

Of those amine compounds, an aliphatic amine and an imide compound having an amino group are preferable, and an aliphatic amine having an alkyl or alkenyl group having 4 to 18 carbon atoms and an N-substituted alkyl(alkenyl)succinimide are more preferable.

The N-substituted alkyl(alkenyl)succinimide, in which a primary amino group on the end of a polyamine serves as a nitrogen atom in an imide group, may have two structures of mono-succinimide including one imide group and di-succinimide including two imide groups. Such N-substituted alkyl (alkenyl)succinimide includes preferably an alkyl or alkenyl group having a mass average molecular weight of 500 to 3,000 and more preferably, because the production thereof becomes easy, an alkenyl group such as a polypropenyl or polybutenyl group having a mass average molecular weight of 500 to 3,000.

In the method of producing a phosphorus molybdenum amine compound of the present invention, the above-mentioned reaction of the phosphorus molybdenum compound with the amine compound may be performed by: mixing under stirring both the compounds at 50 to 100° C. for 1 to 10 hours; and dehydrating the mixture for 30 minutes to 3 hours at the same temperature as above under reduced pressure.

The lubricating oil composition of the present invention is characterized by containing the above phosphorus molybdenum compound and/or phosphorus molybdenum amine compound. The lubricating base oil to be used in the lubricating oil composition of the present invention is not particularly limited, and examples thereof include general lubricating base oils that are conventionally used as lubricating base oils, such as mineral oils, synthetic oils, and mixtures thereof. More specific examples of the lubricating base oils include poly-α-olefins, ethylene-α-olefin copolymers, polybutenes, alkylbenzenes, alkylnaphthalenes, polyalkylene glycols, polyphenyl ethers, alkyl-substituted diphenyl ethers, polyol esters, dibasic acid esters, carbonates, silicone oils, fluorinated oils, synthetic oils such as Gas-to-Liquids (GTL), paraffin-based mineral oils, naphthene-based mineral oils, and purified mineral oils obtained by purifying the mineral oils. Those base oils may be used alone or as a mixture thereof. Of those lubricating base oils, a base oil having a viscosity index of 100 or more is preferably used, and poly-α-olefins, GTL, and purified mineral oils having a viscosity index of 100 or more are more preferably used.

The content of the phosphorus molybdenum compound and/or the phosphorus molybdenum amine compound of the present invention with respect to the total amount of the lubricating oil composition of the present invention is 10 to 200 ppm by mass, preferably 20 to 100 ppm by mass and more preferably 30 to 80 ppm by mass in terms of the phosphorus content (total phosphorus content in the case where the composition contains the two compounds). If the content is 10 ppm by mass or less, the effects as an antioxidant may not be achieved, while if the content exceeds 200 ppm by mass, effects commensurate with the amount may not be achieved, or sludge may be produced.

If a zinc dithiophosphate represented by the following general formula (3) is blended in the lubricating oil composition of the present invention, the antioxidant ability can be further improved:

[Chemical Formula 4]

(3)

where $R^7$ and $R^8$ each represent hydrocarbon groups, and a represents a number of 0 to ⅓.

In the general formula (3), $R^7$ and $R^8$ each represent hydrocarbon groups. Examples of the hydrocarbon groups include alkyl, alkenyl, aryl, cycloalkyl, and cycloalkenyl groups.

Here, examples of the alkyl group include methyl, ethyl, propyl, isopropyl, butyl, isobutyl, secondary butyl, tertiaryl butyl, pentyl, isopentyl, secondary pentyl, neopentyl, tertiary pentyl, hexyl, secondary hexyl, heptyl, secondary heptyl, octyl, 2-ethylhexyl, secondary octyl, nonyl, secondary nonyl, decyl, secondary decyl, undecyl, secondary undecyl, dodecyl, secondary dodecyl, tridecyl, isotridecyl, secondary tridecyl, tetradecyl, secondary tetradecyl, hexadecyl, secondary hexadecyl, staryl, eicosyl, docosyl, tetracosyl, triacontyl, 2-butyloctyl, 2-butyldecyl, 2-hexyloctyl, 2-hexyldecyl, 2-octyldecyl, 2-hexyldodecyl, 2-octyldodecyl, 2-decyltetradecyl, 2-dodecylhexadecyl, 2-hexadecyloctadecyl, 2-tetradecyloctadecyl, and monomethyl branched-isostearyl.

In addition, examples of the alkenyl group include vinyl, allyl, propenyl, isopropenyl, butenyl, isobutenyl, pentenyl, isopentenyl, hexenyl, heptenyl, octenyl, nonenyl, decenyl, undecenyl, dodecenyl, tetradecenyl, and oleyl.

Further, examples of the aryl group include a phenyl, tolyl, xylyl, cumenyl, mesityl, benzyl, phenetyl, styryl, cinnamyl, benzhydryl, trityl, ethylphenyl, propylphenyl, butylphenyl, pentylphenyl, hexylphenyl, heptylphenyl, octylphenyl, nonylphenyl, decylphenyl, undecylphenyl, dodecylphenyl, styrenated phenyl, p-cumylphenyl, phenylphenyl, benzylphenyl, α-naphthyl, and β-naphthyl groups.

In addition, examples of the cycloalkyl group and cycloalkenyl group include cyclopentyl, cyclohexyl, cycloheptyl, methylcyclopentyl, methylcyclohexyl, methylcycloheptyl, cyclopentenyl, cyclohexenyl, cycloheptenyl, methylcyclopentenyl, methylcyclohexenyl, and methylcycloheptenyl groups.

Of those hydrocarbon groups, $R^7$ and $R^8$ are preferably alkyl groups, more preferably secondary alkyl groups. The number of carbon atoms is preferably 3 to 14, more preferably 3 to 10, and most preferably 3 to 8. In addition, $R^1$ and $R^2$ may be the same or different hydrocarbon groups.

In the case where a=O in the general formula (3), the compound is referred to as a neutral zinc dithiophosphate (neutral salt), while in the case where a=⅓, the compound is referred to as a basic zinc dithiophosphate (basic salt). The zinc dithiophosphate is a mixture of the neutral salt and basic salt, and hence a represents a number of 0 to ⅓. Although the number of a varies depending on the method of producing a zinc dithiophosphate, the number is preferably 0.08 to 0.3, more preferably 0.15 to 0.3, and most preferably 0.18 to 0.3. If the number of a becomes larger, the stability in hydrolysis may deteriorate, while if the number of a becomes smaller, the wear resistance of the blended lubricating oil composition may deteriorate. Therefore, the zinc dithiophosphate may be appropriately selected depending on the intended use.

The amount of the zinc dithiophosphate should be determined in consideration of the amount of the phosphorus molybdenum compound and/or phosphorus molybdenum amine compound of the present invention. The zinc dithiophosphate is added so that the total phosphorus content in the lubricating oil composition of the present invention is preferably 800 ppm by mass or less, more preferably 600 ppm by mass or less, and still more preferably 500 ppm by mass or less. If the content exceeds 800 ppm by mass, sludge may be produced, or an exhaust gas catalyst may be adversely affected when the composition is used in oil for gasoline engines. Meanwhile, when the total phosphorus content in the lubricating oil composition of the present invention is 100 ppm by mass or less, the antioxidant ability may become insufficient.

When a phenol-based antioxidant and/or an amine-based antioxidant is blended in the lubricating oil composition of the present invention, the antioxidant ability can be improved. Examples of the phenol-based antioxidant include 2,6-ditertiary-butylphenol (hereinafter, tertiary butyl is abbreviated as t-butyl), 2,6-di-t-butyl-p-cresol, 2,6-di-t-butyl-4-methylphenol, 2,6-di-t-butyl-4-ethylphenol, 2,4-dimethyl-6-t-butylphenol, 4,4'-methylenebis(2,6-di-t-butylphenol), 4,4'-bis(2,6-di-t-butylphenol), 4,4'-bis(2-methyl-6-t-butylphenol), 2,2'-methylenebis(4-methyl-6-t-butylphenol), 2,2'-methylenebis(4-ethyl-6-t-butylphenol), 4,4'-butylidenebis(3-methyl-6-t-butylphenol), 4,4'-isopropylidenebis(2,6-di-t-butylphenol), 2,2'-methylenebis(4-methyl-6-cyclohexylphenol), 2,2'-methylenebis(4-methyl-6-nonylphenol), 2,2'-isobutylidenebis(4,6-dimethylphenol), 2,6-bis(2'-hydroxy-3'-t-butyl-5'-methylbenzyl)-4-methylphenol, 3-t-butyl-4-hydroxyanisole, 2-t-butyl-4-hydroxyanisole, octyl 3-(4-hydroxy-3,5-di-t-butylphenyl)propionate, staryl 3-(4-hydroxy-3,5-di-t-butylphenyl)propionate, oleyl 3-(4-hydroxy-3,5-di-t-butylphenyl)propionate, dodecyl 3-(4-hydroxy-3,5-di-t-butylphenyl)propionate, decyl 3-(4-hydroxy-3,5-di-t-butylphenyl)propionate, octyl 3-(4-hydroxy-3,5-di-t-butylphenyl)propionate, tetrakis{3-(4-hydroxy-3,5-di-t-butylphenyl)propionyloxymethyl}methane, 3-(4-hydroxy-3,5-di-t-butylphenyl)propionic acid glycerin monoester, ester of 3-(4-hydroxy-3,5-di-t-butylphenyl)propionic acid and glycerin monooleyl ether, 3-(4-hydroxy-3,5-di-t-butylphenyl)propionic acid butylene glycol diester, 3-(4-hydroxy-3,5-di-t-butylphenyl)propionic acid thiodiglycol diester, 4,4'-thiobis(3-methyl-6-t-butylphenol), 4,4'-thiobis(2-methyl-6-t-butylphenol), 2,2'-thiobis (4-methyl-6-t-butylphenol), 2,6-di-t-butyl-α-dimethylamino-p-cresol, 2,6-di-t-butyl-4-(N,N'-dimethylaminomethylphenol), bis(3,5-di-t-butyl-4-hydroxybenzyl)sulfide, tris{(3,5-di-t-butyl-4-hydroxyphenyl)propionyl-oxyethyl}isocya nurate, tris(3,5-di-t-butyl-4-hydroxyphenyl)isocyanurate, 1,3,5-tris(3,5-di-t-butyl-4-hydroxybenzyl)isocyanurate, bis{2-methyl-4-(3-n-alkylthiopropionyloxy)-5-t-butylphenyl}sulfide, 1,3,5-tris (4-t-butyl-3-hydroxy-2,6-dimethylbenzyl) isocyanurate, tetraphthaloyl-di(2,6-dimethyl-4-t-butyl-3-hydroxybenzyl-sulfide), 6-(4-hydroxy-3,5-di-t-butylanilino)-2,4-bis(octylthio)-1,3,5-triazine, 2,2-thio-{diethyl-bis-3-(3,5-di-t-butyl-4-hydroxyphenyl)}propionate, N,N'-hexamethylenebis (3,5-di-t-butyl-4-hydroxy-hydrocinnamide, 3,5-di-t-butyl-4-hydroxy-benzyl-phophodiester, bis(3-methyl-4-hydroxy-5-t-butylbenzyl)sulfide, 3,9-bis[1,1-dimethyl-2-{β-(3-t-butyl-4-hydroxy-5-methylphenyl) propionyloxy}ethyl]-2,4,8,10-tetraoxaspiro[5,5]undecane, 1,1,3-tris(2-methyl-4-hydroxy-5-t-butylphenyl)butane, 1,3,5-trimethyl-2,4,6-tris(3,5-di-t-butyl-4-hydroxybenzyl)benzene, and bis{3,3'-bis-(4'-hydroxy-3'-t-butylphenyl}butyric acid)glycol ester.

The phenol-based antioxidant content is preferably 0.01 to 5% by mass, more preferably 0.05 to 4% by mass, still more preferably 0.1 to 3% by mass with respect to the total amount of the lubricating oil composition of the present invention. If the content is less than 0.01% by mass, the effect of the phenol-based antioxidant may not be achieved, while if the content exceeds 5% by mass, effects commensurate with the amount may not be achieved, or sludge may be produced.

Examples of the amine-based antioxidant include: naphthyl amine-based antioxidants such as 1-naphthyl amine, phenyl-1-naphthyl amine, p-octylphenyl-1-naphthyl amine, p-nonylphenyl-1-naphthyl amine, p-dodecylphenyl-1-naphthyl amine, and phenyl-2-naphthyl amine; phenylenediamine-based antioxidants such as N,N'-diisopropyl-p-phenylene diamine, N,N'-diisobutyl-p-phenylene diamine, N,N'-diphenyl-p-phenylene diamine, N,N'-di-β-nephthyl-p-phenylene diamine, N-phenyl-N'-isopropyl-p-phenylene diamine, N-cyclohexyl-N'-phenyl-p-phenylene diamine, N-1,3-dimethylbutyl-N'-phenyl-p-phenylene diamine, dioctyl-p-phenylene diamine, phenylhexyl-p-phenylene diamine, and phenyloctyl-p-phenylene diamine; diphenyl amine-based antioxidants such as dipyridyl amine, diphenyl amine, p,p'-di-n-butyldiphenyl amine, p,p'-di-t-butyldiphenyl amine, p,p'-di-t-pentyldiphenyl amine, p,p'-dioctyldiphenyl amine, p,p'-dinonyldiphenyl amine, p,p'-didecyldiphenyl amine, p,p'-didodecyldiphenyl amine, p,p'-distyryldiphenyl amine, p,p'-dimethoxydiphenyl amine, 4,4'-bis(4-α,α-dimethylbenzoyl)diphenyl amine, p-isopropoxydiphenyl amine, and dipyridyl amine; and phenothiazine-based antioxidants such as phenothiazine, N-methylphenothiazine, N-ethylphenothiazine, 3,7-dioctylphenothiazine, phenothiazine carboxylate, and phenoselenazine.

The amine-based antioxidant content is preferably 0.01 to 5% by mass, more preferably 0.05 to 4% by mass, still more preferably 0.1 to 3% by mass with respect to the total amount of the lubricating oil composition of the present invention. If the content is less than 0.01% by mass, the effect of the amine-based antioxidant may not be achieved, while if the content exceeds 5% by mass, effects commensurate with the amount may not be achieved, or sludge may be produced.

The lubricating oil composition of the present invention may contain known additives for lubricating oil, and the composition may further contain additives such as an wear resistance agents, extreme-pressure agents, oiliness improvers, detergants, dispersants, viscosity index improvers, pour-point depressants, rust inhibitors, corrosion inhibitors, or defoaming agents depending on the intended use in such amounts that do not impair the effect of the present invention. However, in the case of using a phosphorus-based additive selected from those additives, the total phosphorus content in the lubricating oil composition increases, and hence it is necessary to control the content within the range specified in the present invention.

Examples of the wear resistance agent include organic molybdenum compounds such as sulfated oxymolybdenum dithiocarbamate and sulfated oxymolybdenum dithiophosphate. The amount of the wear resistance agent is preferably 30 to 2,000 ppm by mass and more preferably 50 to 1,000 ppm by mass in terms of the molybdenum content with respect to the base oil. However, sulfated oxymolybdenum dithiocarbamate is preferably used as compared with sulfated oxymolybdenum dithiophosphate containing a phosphorus atom, and sulfated oxymolybdenum dithiocarbamate having an alkyl group having 8 to 13 carbon atoms is more preferably used.

Examples of the extreme-pressure agent include: sulfur-based additives such as sulfurized fat and oil, olefin polysulfide, and dibenzyl sulfide; phosphorus-based compounds such as monooctyl phosphate, tributyl phosphate, triphenyl phosphite, tributyl phosphate, and thiophosphate; and organic metallic compounds such as metal thiophosphate, metal thiocarbamate, and acidic metal phosphate. The blending amount of the extreme-pressure agent is preferably 0.01 to 2% by mass and more preferably 0.05 to 1% by mass with respect to the base oil. However, it is preferable to avoid use of a compound containing a phosphorus atom.

Further, examples of the oiliness-improver include: higher alcohols such as oleyl alcohol and stearyl alcohol; fatty acids such as oleic acid and stearic acid; esters such as oleyl glycerin ester, stearylglycerin ester, and laurylglycerin ester; amides such as lauryl amide, oleyl amide, and stearyl amide; amines such as lauryl amine, oleyl amine, and stearyl amine; and ethers such as lauryl glycerin ether and oleyl glycerin ether. The blending amount of the oilness-improver is preferably 0.1 to 5 mass % and more preferably 0.2 to 3 mass % with respect to the base oil.

Examples of the detergent include sulphonates, phenates, salicates, phosphates of calcium, magnesium, and barium, and perbasic salts thereof. Of those, the perbasic salts are preferable. Of the perbasic salts, a salt having a total basic number (TBN) of 30 to 500 mgKOH/g is more preferable. Moreover, a salicate-based cleaning agent containing no phosphorus and sulfur atom is preferable. The amount of the cleaning agent is preferably 0.5 to 10% by mass and more preferably 1 to 8% by mass with respect to the base oil.

Examples of the dispersant include succinimide, succinate, benzylamine, or succinate, which include an alkyl or alkenyl group having a mass average molecular weight of about 500 to 3,000, or boron-denatured products thereof. The blending amount of each dispersant is preferably 0.5 to 10% by mass and more preferably 1 to 8% by mass with respect to the base oil.

Examples of the viscosity index improver include poly(C1-18)alkyl methacrylates, (C1-18)alkyl acrylate/(C1-18)alkyl methacrylate copolymers, diethylaminoethyl methacrylate/(C1-18)alkyl methacrylate copolymers, ethylene/(C1-18) alkyl methacrylate copolymers, polyisobutylenes, polyalkylstyrenes, ethylene/propylene copolymers, styrene/maleate copolymers, and styrene/isoprene hydrogenated copolymers. Alternatively, a dispersible or multifunctional viscosity index improver having dispersion performance may be used. The average molecular weight is about 10,000 to 1,500,000. The blending amount of the viscosity index improver is preferably 0.1 to 20% by mass and more preferably 0.3 to 15% by mass with respect to the base oil.

Further, examples of the pour-point depressant include polyalkyl methacrylate, polyalkyl acrylate, polyalkyl styrene, and polyvinyl acetate. The mass average molecular weight is 1,000 to 100,000. The blending amount of those pour-point depressants is preferably 0.005 to 3 mass % and more preferably 0.01 to 2 mass % with respect to the base oil.

In addition, examples of the rust inhibitor include sodium nitrite, oxidized paraffin wax calcium salt, oxidized paraffin wax magnesium salt, beef tallow fatty acid alkali metal salt, alkali earth metal salt or an amine salt, alkenyl succinic acid or alkenyl succinic acid half ester (molecular weight of alkenyl group is about 100 to 300), sorbitan monoester, nonylphenol ethoxylate, and lanolin fatty acid calcium salt. The blending amount of those rust inhibitors is preferably 0.01 to 3 mass % and more preferably 0.02 to 2 mass % with respect to the base oil.

Further, examples of the corrosion inhibitor include benzotriazole, benzoimidazole, benzothiazole, and tetraalkylthiuram disulfide. The blending amount of the corrosion inhibitor is preferably 0.01 to 3 mass % and more preferably 0.02 to 2 mass % with respect to the base oil.

In addition, examples of the defoaming agent include polydimethyl silicone, trifluoropropyl methylsilicone, colloidal silica, polyalkyl acrylate, polyalkyl methacrylate, alcohol ethoxy/propoxylate, fatty acid ethoxy/propoxylate, and sorbitan partial fatty acid ester. The blending amount of the defoaming agent is preferably 0.001 to 0.1 mass % and more preferably 0.001 to 0.01 mass % with respect to the base oil.

The lubricating oil composition of the present invention can suppress the increase in the concentration of phosphorus atoms having various adverse effects and can enhance the antioxidant ability. Phosphorus atom content may vary depending on the intended use and use environment, and the content is preferably 800 ppm by mass or less with respect to the total amount of the lubricating oil composition. However, there may be some cases where problems are not caused even if the phosphorus content exceeds 800 ppm by mass in a lubricating oil for diesel-powered vehicles not equipped with an exhaust gas catalyst. In those cases, if the phosphorus molybdenum compound or phosphorus molybdenum amine compound of the present invention is added to the oil, the antioxidant ability of the lubricating oil composition can be drastically improved as compared with an oil containing no additive.

The lubricating oil composition containing the phosphorus molybdenum compound and/or phosphorus molybdenum amine compound obtained by the production method of the present invention can be used for lubrication in any application including, for example, lubricating oils such as engine oil, gear oil, turbine oil, hydraulic oil, fire-resistant fluid, refrigerant oil, compressor oil, vacuum pump oil, bearing oil, insulating oil, sliding surface oil, rock drill oil, metalworking fluid, plastic working oil, heat treating oil, and grease. Of those, the lubricating oil composition can be suitably used for engine oil and turbine oil, those of which are used in harsh circumstances and required to have the antioxidant ability.

EXAMPLES

Hereinafter, the present invention is described more specifically by way of examples. In the following examples, the terms "%" and "ppm" mean "% by mass" and "ppm by mass", respectively, unless otherwise stated. Compounds to be used in the examples were synthesized by the following methods.

Example 1

Production Example of Phosphorus Molybdenum Compound 1

In a 3,000-ml flask equipped with anitrogen introduction tube, a reflux tube, a stirrer, and a thermometer, 1 mol (242 g) of sodium molybdate dihydrate was dissolved in 206 g of water, and 0.5 mol (54 g) of thiourea dioxide was added thereto under a nitrogen stream at 50 to 60° C., followed by a reaction for 1 hour. Subsequently, 2 mol of 20% sulfuric acid (980 g) was added dropwise over 1 hour, and aging was performed for 2 hours. After aging, the mixture was cooled to 30 to 40° C., and 1 mol of dioleyl phosphate (598 g) was added dropwise over 1 hour, followed by a further reaction for 10 hours. 300 ml of n-hexane was added to the resultant product, and the mixture was stirred for 30 minutes. Thereafter, the mixture was allowed to stand for 1 hour to separate the mixture into an aqueous phase and an oil phase, and the aqueous phase was removed. Finally, the solvent was removed from the resultant oil phase under reduced pressure, to thereby obtain 711 g of a dark brown oily product (Phosphorus Molybdenum Compound 1). From the results of analysis of the resultant dark brown oily product, the molybdenum content and the phosphorus content were found to be 12.2% and 4.2%, respectively. The yield of molybdenum was found to be 90%.

Example 2

Production Example of Phosphorus Molybdenum Compound 2

The procedures of Example 1 were repeated except for replacing 1 mol of dioleyl phosphate with a mixture of 0.5 mol of monooctyl phosphate and 0.5 mol of dioctyl phosphate, and except for replacing 0.5 mol of thiourea dioxide with 0.17 mol of hydrosulfite, to thereby obtain 568 g of a dark blue oily product (Phosphorus Molybdenum Compound 2). The molybdenum content and phosphorus content were found to be 21.0% and 7.2%, respectively. The yield of molybdenum was found to be 88%.

Example 3

Production Example of Phosphorus Molybdenum Compound 3

In the same reaction apparatus as in Example 1, 144 g of water was added to 1 mol (144 g) of molybdenum trioxide, and the mixture was heated to 50 to 60° C. under a nitrogen stream. Then, 1 mol (200 g) of 20% sodium hydroxide was added dropwise over 1 hour, followed by aging for 1 hour. After aging, 0.5 mol (54 g) of thiourea dioxide was added to react the mixture for 1 hour. Subsequently, 2 mol of 20% sulfuric acid (980 g) was added dropwise over 1 hour, followed by further aging for 2 hours. The mixture was cooled to 40 to 50° C., and a mixture of 0.5 mol of monooctyl phosphate and 0.5 mol of dioctyl phosphate (266 g) was added dropwise over 1 hour, followed by a reaction for 10 hours. 300 ml of n-hexane was added, and the mixture was stirred for 30 minutes and allowed to stand for 1 hour to separate the mixture into an aqueous phase and an oil phase, followed by removal of the aqueous phase. Finally, the solvent was removed from the resultant oil phase under reduced pressure, to thereby obtain 401 g of a dark brown oily product (Phosphorus Molybdenum Compound 3). The molybdenum content and phosphorus content were found to be 22.5% and 7.7%, respectively. The yield of molybdenum was found to be 94%.

Example 4

Production Example of Phosphorus Molybdenum Compound 4

The procedures of Example 3 were repeated except for replacing the mixture of 0.5 mol of monooctyl phosphate and 0.5 mol of dioctyl phosphate with 1 mol of dioleyl phosphate, to thereby obtain 440 g of a dark brown oily product (Phosphorus Molybdenum Compound 4). The molybdenum content and phosphorus content were found to be 20.1% and 6.9%, respectively. The yield of molybdenum was found to be 92%.

Example 5

Production Example of Phosphorus Molybdenum Compound 5

The procedures of Example 3 were repeated except for replacing the mixture of 0.5 mol of monooctyl phosphate and 0.5 mol of dioctyl phosphate with 1 mol of monooleyl phosphate, to thereby obtain 340 g of a dark brown oily product (Phosphorus Molybdenum Compound 5). The molybdenum content and phosphorus content were found to be 26.3% and 9.1%, respectively. The yield of molybdenum was found to be 93%.

Example 6

Production Example of Phosphorus Molybdenum Compound 6

The procedures of Example 3 were repeated except for replacing the mixture of 0.5 mol of monooctyl phosphate and 0.5 mol of dioctyl phosphate with a mixture of 0.5 mol of mono-4-isopropylphenyl phosphate and 0.5 mol of di-4-isopropylphenyl phosphate, to thereby obtain 401 g of a dark brown oily product (Phosphorus Molybdenum Compound 6). The molybdenum content and phosphorus content were found to be 22.2% and 7.6%, respectively. The yield of molybdenum was found to be 93%.

Example 7

Production Example of Phosphorus Molybdenum Compound 7

The procedures of Example 3 were repeated except that the amount of thiourea dioxide was increased to 2 mol, to thereby obtain 395 g of a dark brown oily product (Phosphorus Molybdenum Compound 7). The molybdenum content and phosphorus content were found to be 22.6% and 7.7%, respectively. The yield of molybdenum was found to be 93%.

Example 8

Production Example of Phosphorus Molybdenum Amine Compound 1

The Phosphorus molybdenum Compound 1 obtained in Example 1 (711 g) was reacted with 2 mol of monooleylamine (534 g) at 60 to 70° C. for 4 hours. The mixture was further stirred under reduced pressure of 2.3 to 1.3 kPa for 1 hour, to thereby obtain 1,224 g of a dark blue oily product (Phosphorus Molybdenum Amine Compound 1). The molybdenum content and phosphorus content were found to be 7.0% and 2.4%, respectively. The yield of molybdenum was found to be 99%.

Example 9

Production Example of Phosphorus Molybdenum Amine Compound 2

The Phosphorus molybdenum Compound 3 obtained in Example 3 (401 g) was reacted with 1 mol of dioctylamine (241 g) at 60 to 70° C. for 4 hours. The mixture was further stirred under reduced pressure of 2.3 to 1.3 kPa for 1 hour, to thereby obtain 631 g of a dark brown oily product (Phosphorus Molybdenum Amine Compound 2). The molybdenum content and phosphorus content were found to be 14.2% and 4.9%, respectively. The yield of molybdenum was found to be 99%.

Example 10

Production Example of Phosphorus Molybdenum Amine Compound 3

The Phosphorus molybdenum Compound 4 obtained in Example 4 (440 g) was reacted with 1.2 mol of alkenyl monosuccinate polyimide (737 g) at 60 to 70° C. for 4 hours. The mixture was further stirred under reduced pressure of 2.3 to 1.3 kPa for 1 hour, to thereby obtain 1,153 g of a dark brown oily product (Phosphorus Molybdenum Amine Compound 3). The molybdenum content and phosphorus content were found to be 7.5% and 2.6%, respectively. The yield of molybdenum was found to be 98%.

Comparative Example 1

In a 3,000-ml flask equipped with a nitrogen introduction tube, a reflux tube, a stirrer, and a thermometer, 1 mol (206 g) of sodium molybdate was dissolved in 206 g of water, and 0.5 mol of thiourea dioxide was added thereto under a nitrogen stream at 50 to 60° C., followed by a reaction for 1 hour. Subsequently, the mixture was cooled to 30 to 40° C., and 2 mol of dioctyl phosphate (644 g) was added dropwise over 1 hour. Then, 1 mol of 20% sulfuric acid was added dropwise over 1 hour. Thereafter, the temperature was raised to 100° C., and a reaction was performed for 10 hours. 300 ml of n-hexane was added to the resultant, and the mixture was stirred for 30 minutes. Thereafter, the resultant mixture was allowed to stand for 1 hour to separate the mixture into an aqueous phase and an oil phase, and the aqueous phase was removed. Finally, the solvent was removed from the resultant oil phase under reduced pressure, to thereby obtain 437 g of a dark blue oily product (Comparative Product 1). From the results of the analysis of the resultant dark blue oily product, the molybdenum content and the phosphorus content were found to be 19.5% and a of 13.5%, respectively. The yield of molybdenum was found to be 89%.

Comparative Example 2

The procedures of Comparative Example 1 were repeated except for replacing 0.5 mol of thiourea dioxide with 0.17 mol of hydrosulfite, and except for replacing 2 mol of dioctyl phosphate with the mixture of 0.5 mol of monooctyl phosphate and 0.5 mol of dioctyl phosphate, to thereby obtain 359 g of a dark blue oily product (Comparative Product 2). The molybdenum content and the yield of molybdenum were found to be 16.6% and 62%, respectively. The phosphorus content was found to be 8.1%.

Figure 1:
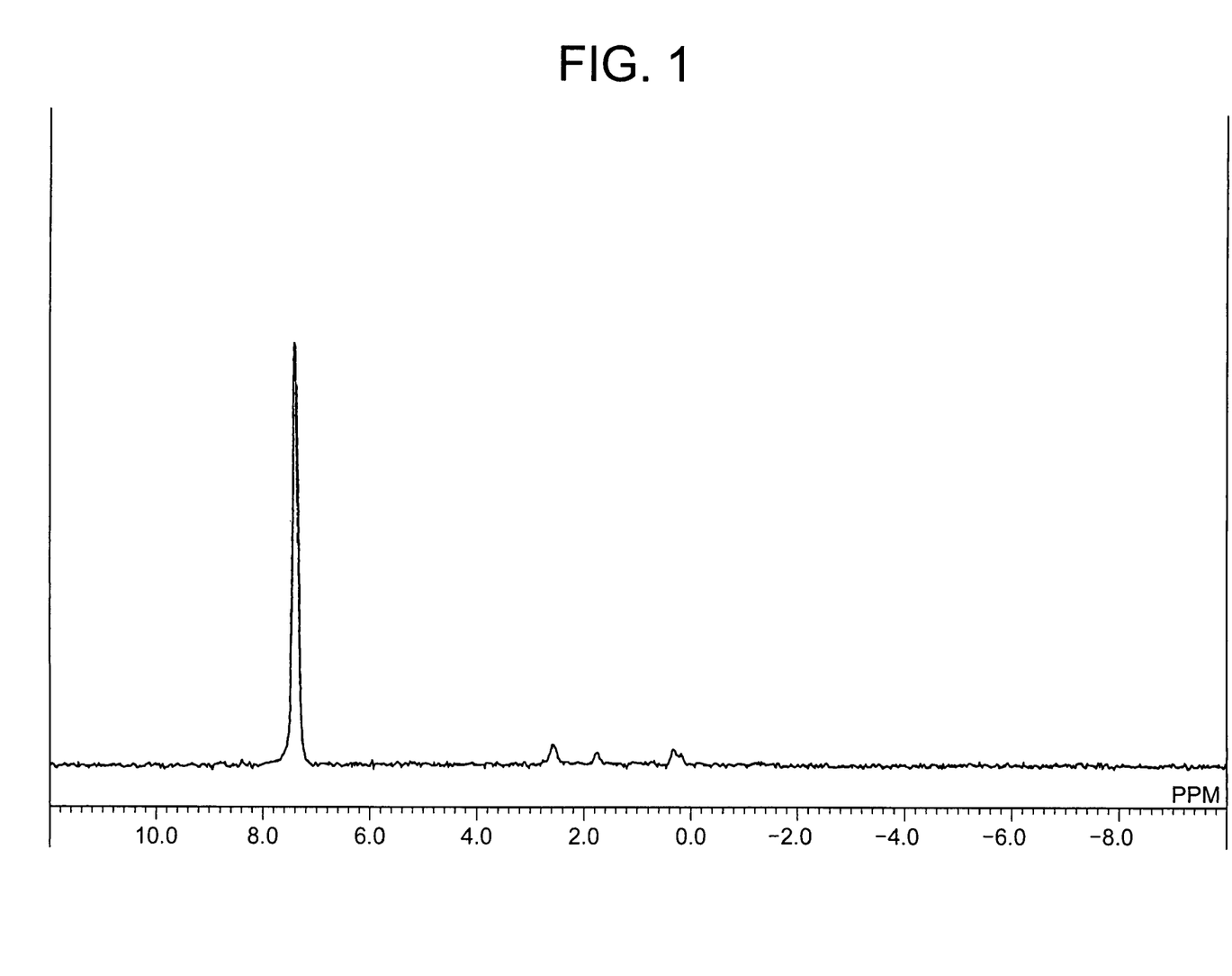
FIG. 1 is a phosphorus$^{31}$-NMR chart of Compound 2.
Figure 2:
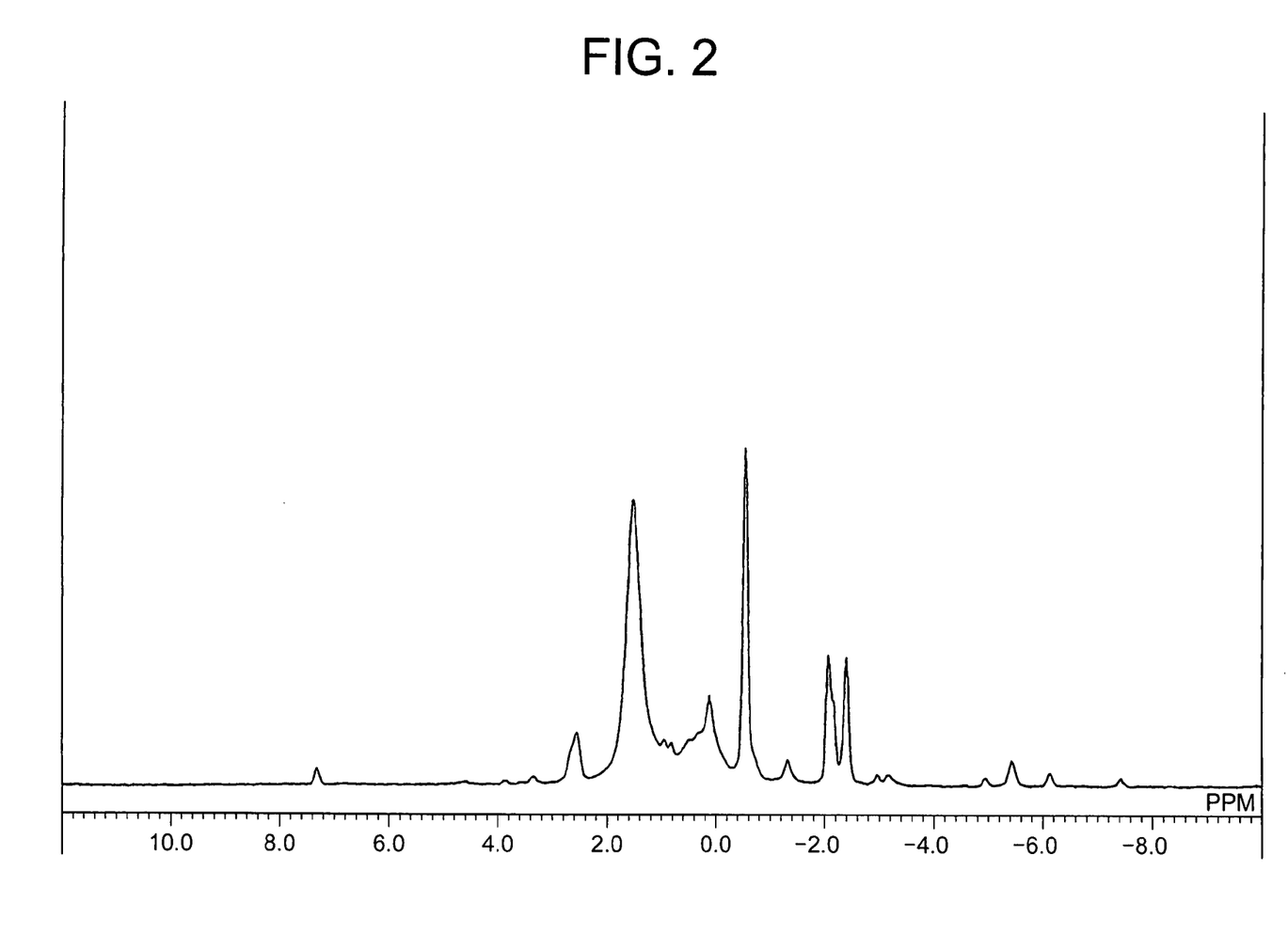
FIG. 2 is a phosphorus$^{31}$-NMR chart of Comparative Product 2.

The Phosphorus molybdenum Compound 2 and Comparative Product 2, which were produced by the different methods using the same materials, were analyzed by phosphorus[31]-NMR using JNM-LA400 (JEOL DATUM LTD.) to compare the difference in their structures. The results thereof are shown in FIGS. 1 and 2. In addition, the molybdenum contents and phosphorus contents of the compounds were also compared.

Phosphorus molybdenum Compound 2: Mo content 21.0% by mass, phosphorus content 7.2% by mass Comparative Product 2

Mo Content 16.6% by Mass, Phosphorus Content 8.1% by Mass

The results reveal that the Phosphorus molybdenum Compound 2 and Comparative Product 2 are different from each other.

Structural Analysis of Phosphorus Molybdenum Compound

The Phosphorus Molybdenum Compound 4 produced as above was washed with n-hexane and water three times, and the solvent was removed under reduced pressure to increase the purity. The resultant Phosphorus Molybdenum Compound 4 was subjected to structural analysis:

<Elemental Analysis>

C: 42.6%, H, 7.6%, Mo: 21.4%, P: 6.9%.

From the comparison of the analysis values of the Phosphorus molybdenum Compound 4 before and after purification, the molybdenum content in the Phosphorus Molybdenum Compound 4 was found to increase after purification. The results suggest that any acidic phosphate not bound to a molybdenum atom is removed by purification, thereby decreasing the total amount of the compound and relatively increasing the molybdenum content. In addition, it was estimated that the unbound phosphorus atoms in the acidic phosphate are removed by purification, and hence no changes occur in the phosphorus content. The results of the elemental analysis reveal that the molybdenum atoms and phosphorus atoms are present in an equal molar ratio. From the facts that there are molybdenum atoms and phosphorus atoms in an equal molar ratio and that the molybdenum atoms are reduced to pentavalent molybdenum atoms, the phosphorus molybdenum compound is estimated to have the following structure as a basic skeleton.

[Chemical Formula 5]

(3)

<TOF-MS Analysis>

TOF-MS analysis was performed using a time-of-flight mass analyzer, which determines molecular weight by ionizing a sample to fly the sample at a constant distance and measuring the flight time. The molecular weight of the Phosphorus molybdenum Compound 4 was determined using a Vayager-DE STR (Perseptive Biosystems) as a TOF-MS analyzer. A mixture of the following three solutions was used as a sample.

Figure 3:
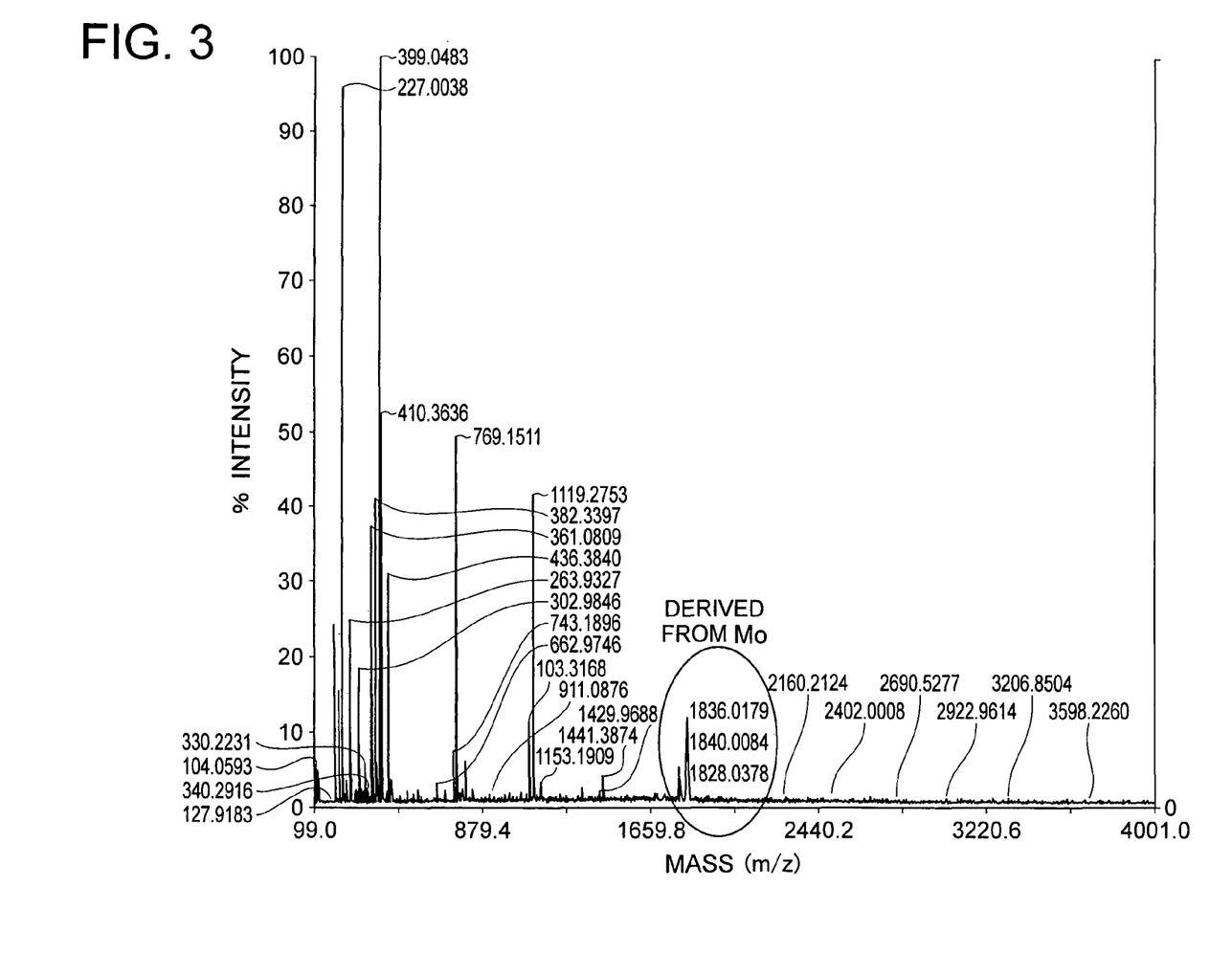
FIG. 3 is a TOF-MS analysis chart of Compound 4.
Figure 4:
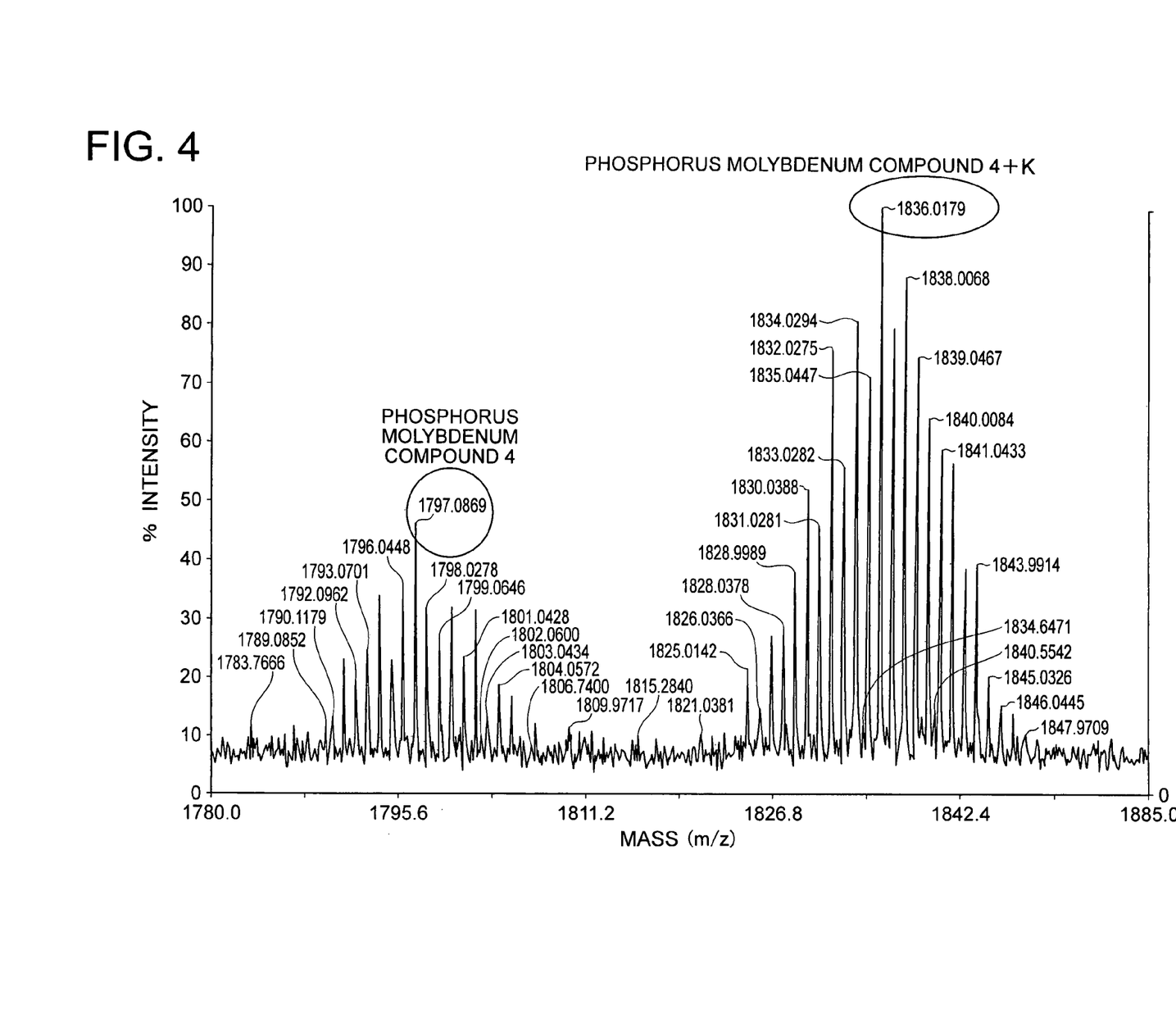
FIG. 4 is a partially magnified view of the TOF-MS analysis chart of FIG. 3.

(1) Solution of the Phosphorus molybdenum Compound 4 in 1% THF: 2 μl
(2) Solution of dithranol (matrix substance: 1,8-dihydroxy-9,10-dihydroanthracene-9-one): 20 μl
(3) Potassium trifluoroacetate: 0.05 μl Note that when the solution (3) was added, a peak of the total of the molecular weights of the Phosphorus molybdenum Compound 4 and potassium appears. This is useful for confirming whether the peak is false or not. The resultant charts are shown in FIGS. 3 and 4.

<Results of TOF-MS Analysis>

Molybdenum atoms have many isotopes, but there is no isotope having a particularly high abundance ratio. Main atomic weights and their ratios are as follows: 92:14.84%, 94:9.25%, 95:15.92%, 96:16.68%, 97:9.55%, 98:24.13%.

In the TOF-MS analysis, a molecule having a molecular weight different from the others by 1 is recognized as a different peak. Therefore, in a chart of a compound containing molybdenum, peaks representing different molecular weights appear. The chart of FIG. 3 shows the results of the TOF-MS analysis, and detail investigation of the peaks reveals that peaks specific to molybdenum are present only at molecular weights of about 1,800. There is no peak present at a molecular weight larger than that of molybdenum, and hence this is considered to be the Phosphorus Molybdenum Compound 4. The peaks present at lower molecular weights are peaks of phosphates or the like obtained by decomposing the Phosphorus Molybdenum Compound 4.

The chart of FIG. 4 is an enlarged version of the peaks of the molecular weights of about 1,800 in the chart of FIG. 3. There are two peak groups specific to molybdenum atom, and the difference in the molecular weights of the two groups is 39. Therefore, the right group corresponds to the total of the left group and potassium. Accordingly, the left group represents the molecular weight of the Phosphorus Molybdenum Compound 4.

The largest molecular weight in the left group is about 1,797, which is just four times the molecular weight of the basic skeleton determined by the elemental analysis. If four basic skeletons were linked to each other, molybdenum atoms and oxygen atoms are alternately arranged to form a ring, resulting in the following structure:

[Chemical Formula 6]

The molecular formula of the Phosphorus molybdenum Compound 4 is $C_{64}H_{136}Mo_4P_4$ and the molecular weight thereof is 1797.44. In addition, the theoretic element ratio is as follows: C, 42.77%; H, 7.63%; Mo, 21.35%; and P, 6.89%. The theoretic element ratio is identical with the measured element analytical value: C, 42.6%; H, 7.6%; Mo, 21.4%; P, 6.9%. The analyzed Phosphorus Molybdenum Compound 4 may have the above-mentioned structure.

Compound 11: zinc dithiophosphate (phosphorus content 8.2%, in the general formula (3), $R^1$=n-butyl, $R^2$=1-octyl, a=0.2)

Compound 12: p,p'-didodecyldiphenyl amine

Compound 13: octyl 3-(4-hydroxy-3,5-di-t-butylphenyl)propionate

<Peroxide Decomposition Test>

For the Phosphorus molybdenum Compounds 1 to 7, phosphorus molybdenum amine compounds 8 to 10, Comparative Products 1 and 2, and Compound 11 (zinc thiophosphate), the secondary oxidation-preventing abilities were evaluated by the following method. To a 100-ml autoclave including a glass inner cylinder tube, 37.5 g of toluene, 2.5 g of cumene hydroperoxide (hereinafter, abbreviated as CHP), and each of the above-mentioned compounds were added so that the mixture has a phosphorus content of 50 ppm by mass, followed by sealing. The autoclave was placed in a 70° C. shaking constant-temperature bath, followed by shaking at 70 times/min. 4 hours later, a sample was taken, and the peroxide value was measured to analyze the amount of residual CHP. The amount of residual CHP is represented as a percentage with respect to the initial amount of CHP. The amount of phenol, which was produced by the action of the compound as a secondary antioxidant, was determined by gas chromatography. The amount of phenol produced by ion decomposition of the total amount of cumene hydroperoxide added first was defined as 100%, and the results are represented as percentages with respect to the total amount. Table 1 shows the results.

CHP produces phenol by ion decomposition and produces cumyl alcohol, acetophenone, or the like by radical decomposition via various radicals. Production of radicals is not preferable from the viewpoint of preventing oxidation, and hence a production of larger amount of phenol suggests that the compound has higher antioxidant ability.

<Measurement of Sludge Amount>

The above-mentioned compounds were dissolved in mineral oil-based high-viscosity-index (VI) oil having dynamic viscosities of 4.24 mm$^2$/s (at 100° C.) and 19.65 mm$^2$/s (at 40° C.) and a viscosity index of 126 so that each of the resultant mixtures had a Mo content of 100 ppm by mass. In conformance with the ISOT test specified in item 4 of JIS K 2514-1993 (lubricating oil-oxidation stability testing method), the test oils were degraded. The test was performed as follows: 250 ml of each test oil were placed into a glass vessel having incorporated therein a copper plate and an iron plate as catalysts, and the whole was heated at 165.5° C. for 168 hours to degrade the test oil by oxidation while the sample was stirred at 1,300 rpm in such a manner that air would be mixed in. After completion of the test, the all of the test oil was filtered to separate sludge produced, and the sludge was washed with toluene and dried. Then, the weight of the sludge was measured. Table 1 shows the results.

TABLE 1

|  | Compound | Residual CHP amount (%) | Phenol amount (%) | Sludge amount (%) |
|---|---|---|---|---|
| Example | Phosphorus Molybdenum Compound 1 | 12.0 | 81.1 | 0.223 |
|  | Phosphorus Molybdenum Compound 2 | 7.5 | 85.8 | 0.121 |
|  | Phosphorus Molybdenum Compound 3 | 6.8 | 88.3 | 0.119 |
|  | Phosphorus Molybdenum Compound 4 | 10.8 | 83.2 | 0.119 |
|  | Phosphorus Molybdenum Compound 5 | 12.3 | 82.0 | 0.210 |
|  | Phosphorus Molybdenum Compound 6 | 8.2 | 87.2 | 0.118 |
|  | Phosphorus Molybdenum Compound 7 | 7.0 | 87.8 | 0.121 |
|  | Phosphorus Molybdenum Amine Compound 8 | 14.5 | 76.1 | 0.116 |
|  | Phosphorus Molybdenum Amine Compound 9 | 13.3 | 77.5 | 0.117 |
|  | Phosphorus Molybdenum Amine Compound 10 | 11.3 | 79.8 | 0.114 |
| Comparative Example | Comparative Product 1 | 43.3 | 45.6 | 0.133 |
|  | Comparative Product 2 | 44.7 | 46.8 | 0.141 |
|  | Compound 11 | 21.1 | 15.6 | 0.122 |

Example 11

In a glass inner cylinder tube, each of the above-mentioned compounds were added to 5 g of a base oil in combination as shown in Table 2, and the mixture was stirred to disperse/dissolve the compound. Then, the tube was placed into a 100-ml autoclave, followed by sealing with a lid equipped with a pressure sensor and an exhaust pipe. Air in the autoclave was exhausted via the exhaust pipe using a vacuum pump, and oxygen was supplied so that the autoclave was in a 100% oxygen atmosphere at a pressure of 101 kPa. The autoclave was placed in a 160° C. constant-temperature bath, and the pressure was measured every hour to determine the time between the start of the test and the moment when the pressure reached a level lower than 80 kPa as an oxidation induction period. Oxidation degradation causes a reduction in the pressure due to consumption of oxygen, and hence a longer oxidation induction period suggests that the composition has higher antioxidant ability. Table 2 shows the results.

Note that the base oil used was the same as the mineral oil-based high-viscosity-index (VI) oil used in <Measurement of sludge amount> above.

TABLE 2

|  | Amounts of Additive Blended (mg) | | | | Phosphorus content (ppm by mass) | Oxidation induction period (hrs) |
|---|---|---|---|---|---|---|
| Example | Compound 2 2.5 | | | | 27 | 80 |
|  | Compound 3 2.5 | | | | 38 | 82 |
|  | Compound 4 2.5 | | | | 34 | 87 |
|  | Compound 8 2.5 | | | | 12 | 72 |
|  | Compound 10 2.5 | | | | 13 | 74 |
|  | Compound 10 7.0 | | | | 36 | 83 |
|  | Compound 2 2.5 | Compound 11 28.5 | | | 494 | 134 |
|  | Compound 10 2.5 | Compound 11 28.5 | | | 480 | 130 |
|  | Compound 2 2.5 | Compound 11 28.5 | Compound 12 12.5 | | 494 | 200 or more |
|  | Compound 2 2.5 | Compound 11 28.5 | Compound 13 12.5 | | 494 | 200 or more |
|  | Compound 2 2.5 | Compound 11 28.5 | Compound 12 12.5 | Compound 13 12.5 | 493 | 200 or more |
| Comparative Example | Comparative Product 1 2.5 | | | | 68 | 32 |
|  | Comparative Product 2 2.5 | | | | 40 | 34 |
|  | Comparative Product 2 2.5 | Compound 11 28.5 | | | 508 | 79 |
|  | Comparative Product 2 2.5 | Compound 11 28.5 | Compound 12 12.5 | Compound 13 12.5 | 505 | 98 |
|  | Comparative Product 11 2.5 | Compound 12 12.5 | Compound 13 12.5 | | 467 | 81 |

In Table 2, the term "200 or more" in the oxidation induction period means that the pressure did not lower to 80 kPa even after 200 hours.

Example 12

Gasoline engine oil compositions (Base oils A and B) and a diesel engine oil composition (Base oil C) were each compounded, and the above-mentioned compounds shown in Table 4 were dissolved therein in amounts shown in Table 4 with respect to 100 parts by mass of each of the oils. The resultant test oils were subjected to the ISOT test as shown in Example 2 to degrade the oils by oxidation, and the increases in the total acid numbers of the degraded oils (values obtained by subtracting the total acid numbers of the test oils before degradation from the total acid numbers of the degraded oils) were determined. An oil with less increase in the total acid number indicates higher oxidative stability. In this test, if the increase in the total acid number exceeds 10 mgKOH/g, the oil is difficult to be used as a general engine oil. Table 3 shows the formulations of the gasoline engine oil compositions and diesel engine oil composition, and Table 4 shows the test results. The base oils used are the same as the mineral oil-based high-viscosity-index (VI) oil used in Example 2.

TABLE 3

| | Base oil A | Base oil B | Base oil C |
|---|---|---|---|
| Base oil | 100 parts by mass | 100 parts by mass | 100 parts by mass |
| Methacrylate-based viscosity index improver | 3.4 parts by mass | 3.4 parts by mass | 4.2 parts by mass |
| Succinimide-based dispersant | 5 parts by mass | 5 parts by mass | 10 parts by mass |
| Sulfonate-based cleaning agent | 2.5 parts by mass | 2.5 parts by mass | 5 parts by mass |
| Compound 11 | 1.0 part by mass | 0.63 part by mass | 1.5 parts by mass |
| Compound 12 | 0.25 part by mass | 0.25 part by mass | 0.25 parts by mass |
| Compound 13 | 0.25 part by mass | 0.25 part by mass | 0.25 parts by mass |
| Phosphorus content (ppm by mass) | 729 | 461 | 1,015 |

TABLE 4

| | Compound | Blending amount of compound (part by mass) | Base oil A Acid number (mgKOH/g)/ phosphorus content (ppm by mass) | Base oil B Acid number (mgKOH/g)/ phosphorus content (ppm by mass) | Base oil C Acid number (mgKOH/g)/ phosphorus content (ppm by mass) |
|---|---|---|---|---|---|
| Example | Compound 2 | 0.5 | 4.1/754 | 4.9/486 | 3.0/1,040 |
| | Compound 10 | 1.0 | 4.7/755 | 5.2/487 | 3.7/1,041 |
| Comparative Example | Comparative Product 2 | 0.5 | 10.2/770 | 12.7/500 | 8.8/1,055 |
| | None | — | 18.2/729 | 20.1/461 | 16.8/1,015 |

As described above, the inventors of the present invention have succeeded in producing an engine oil composition having a phosphorus content of 800 ppm by mass or less or 500 ppm by mass or less, which is tolerable in general use, by blending the phosphorus molybdenum compound or phosphorus molybdenum amine compound of the present invention. Moreover, even in an engine oil composition having a phosphorus content of 1,000 ppm by mass or more, significant antioxidant effect has been achieved.

The invention claimed is:

1. A method of producing a phosphorus molybdenum compound represented by the following general formula (I):

[Chemical Formula 1]

(1)

where $R^1$ to $R^6$ each independently represent a hydrogen atom or a hydrocarbon group, and p represents a number of 1 to 5, provided that all of $R^1$ to $R^6$ cannot all be hydrogen atoms at the same time, comprising: reducing a hexavalent molybdenum compound with a reducing agent; neutralizing the resultant with a mineral acid; and reacting the resultant with an acidic phosphate.

2. A method of producing a phosphorus molybdenum compound according to claim 1, wherein the acidic phosphate is at least one member selected from the group consisting of a monophosphate having an alkyl group with 4 to 18 carbon atoms and a diphosphate having an alkyl group with 4 to 18 carbon atoms.

3. A method of producing a phosphorous molybdenum compound according to claim 1, wherein p is 2.

* * * * *